United States Patent [19]

Henderson et al.

[11] Patent Number: 5,362,749
[45] Date of Patent: Nov. 8, 1994

[54] MOLLUSCICIDES

[75] Inventors: Ian F. Henderson, Harpenden; Joseph I. Bullock, Guildford; Geoffrey G. Briggs, Harpenden; Leslie F. Larkworthy, South Croydon, all of England

[73] Assignee: British Technology Group Limited, England

[21] Appl. No.: 945,006

[22] Filed: Sep. 15, 1992

Related U.S. Application Data

[63] Continuation of Ser. No. 510,609, Apr. 18, 1990, abandoned, which is a continuation of Ser. No. 231,181, Aug. 11, 1988, abandoned.

[30] Foreign Application Priority Data

Aug. 11, 1987 [GB] United Kingdom ............... 8719006

[51] Int. Cl.$^5$ .............................................. A61K 31/28
[52] U.S. Cl. ..................................... 514/492; 424/84; 514/502; 514/644; 514/645
[58] Field of Search ............... 424/84; 514/492, 502, 514/644, 645

[56] References Cited

U.S. PATENT DOCUMENTS

| | | | |
|---|---|---|---|
| 2,363,852 | 7/1941 | Beckler | 167/48 |
| 3,303,090 | 2/1967 | Huffman et al. | 167/22 |
| 3,622,674 | 11/1971 | Butler | 424/289 |
| 4,132,780 | 1/1979 | McConnell | 424/127 |
| 4,613,616 | 9/1986 | Winston et al. | 514/507 |

FOREIGN PATENT DOCUMENTS 1530315 6/1968 France .............. A01N 113/274
2320063 10/1963 Japan .

OTHER PUBLICATIONS

"Structure and Activity in Molluscicides. Effect of Chelation," I. Nabith, M. T. El-Wassimi, M. M. Kamel and J. Metri. *Journal of Medicinal Chemistry*, 2, No. 2, 177–189 (1975).

"Chemical Chelation Reactions in Fresh Water Snails, Intermediate Hosts for Schistosomiasis," I. Nabih, M. Khater and E. Farrag. *Cellular and Molecular Biology*, 30(2), 120–132 (1984).

"Effects of Cu, Cd, V in Physa Acuta (Draparnaud)," E. Piccinni, O. Coppellotti, L. Giannoni and O. Ravera. *Environmental Technology Letters*, vol. 6, pp. 505–513 (1985).

"Use of Copper as a Molluscicide," Thomas C. Cheng. *Copper in the Environment Part II: Health Effects*, pp. 401–432 ed. J. O. Nriagee, Pub. John Wiley, New York 1979.

BCPC Mon. No. 41 Slugs and Snails in World Agriculture—A New Group of Molluscicidal Compounds, I. F. Henderson, G. G. Briggs, N. P. Coward, G. W. Dawson and J. A. Pickett, pp. 289–294.

Stoner et al. CA 84:85406u 1976.

*Primary Examiner*—Marianne M. Cintins
*Assistant Examiner*—Russell Travers
*Attorney, Agent, or Firm*—Rosenman & Colin

[57] ABSTRACT

The use as a molluscicide of a chelate of aluminium (III) with a ligand of formula I or of iron (III) with a ligand of formula II $$[R^1COCHCOR^2]^-  \quad\quad  I$$

$$[R^3NO.N=O]^-  \quad\quad  II$$

wherein formulae II: $R^3$ represents:
  $C_1$–$C_6$ alkyl, provided that when the alkyl group contains more than four carbon atoms the group is a branched chain alkyl group.

16 Claims, No Drawings

MOLLUSCICIDES

CROSS-REFERENCE

This is a continuation of Ser. No. 510,609 filed Apr. 18, 1990, now abandoned which is a continuation of Ser. No. 231,181 filed Aug. 11, 1988, now abandoned.

This invention relates to molluscicides and in particular to slug and snail poisons.

Accordingly the present invention comprises the use as a molluscicide of a chelate of aluminium (III) with a ligand of formula I or, of iron (III) with a ligand of formula II $$[R^1COCHCOR^2]^-  \quad I$$

$$[R^3NO.N=O]^-  \quad II$$

in which formulae:

$R^1$ and $R^2$, which may be identical or different, represent: methyl, ethyl, propyl, methoxyethyl, ethoxyethyl, dimethoxy methyl or diethoxymethyl and $R^3$ represents: $C_1$-$C_6$ alkyl, provided that when the alkyl group contains more than four carbon atoms the group is a branched chain alkyl group.

In general, chelates comprising three bidentate ligands, which may be identical or different, though which usually are identical, are preferred and especially those which lose one ligand molecule or ion to form a bis cation as shown for example in the following equation wherein $acac^{31}$ represents $[CH_3COCH\ COCH_3]$.

$$Al^{III}(acac)_3 \rightleftharpoons Al^{III}(acac)_2{}^+ + acac^-$$

$$Al^{III}(acac)_2{}^+ \rightleftharpoons Al^{III}(acac)^{2+} + acac^-$$

$$Al^{III}(acac)^{2+} \rightleftharpoons Al^{3+} + acac^-$$

The ligands of formulae I and II are readily derived respectively from compounds of formula IA: $R^1COCH_2COR^2$ and IIA $R^3NOH.N=O$, by loss of a proton. In chelates comprising ligands of formula I when at least one of $R^1$ and $R^2$ is an alkyl group, the group is preferably unbranched. The $Al^{III}$ chelate in which $R^1$ and $R^2$ both represent methyl is especially preferred.

In chelates comprising ligands of formula II it is preferred that $R^3$ contains no more than four carbon atoms, $R^3$ is preferably methyl, ethyl or D-propyl and the chelate is preferably a trischelate of $Fe^{III}$ comprising identical ligands.

The following compounds of formula IA and IIA are of particular interest:

IA:
  $CH_3COCH_2COCH_3$
  $CH_3CH_2COCH_2COCH_3$
  $CH_3CH_2COCH_2COCH_2CH_3$
  $CH_3COCH_2COCH_2CH_2CH_3$
  $CH_3COCH_2COCH(OCH_3)_2$

IIA:
  $Ch_3NOH.N=O$
  $CH_3CH_2NOH.N=O$
  $CH_3CH_2CH_2NOH.N=O$
  $(CH_3)_2CHNOH.N=O$
  $CH_3(CH_3)_2CH_2NOH.N=O$
  $CH_3CH_2CH(CH_3)NOH.N=O$
  $(CH_3)_2CH_2CH_2NOH.N=O$

The ligands and chelates hereinbefore described may be synthesised by modification of well established routes. Synthesis of complexes comprising the ligand II may be accomplished through the following route $$Mg + R^3X \longrightarrow R^3MgX$$

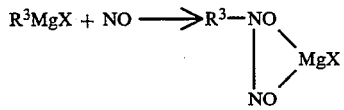

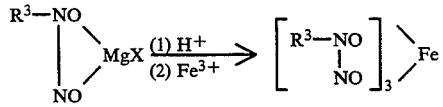

In the foregoing formulae X represents halogen e.g. bromine or iodine.

The present chelates of the present invention may be utilised by formulation as contact poisons or in mollusc baits.

Accordingly the present invention further includes within its scope a contact poison or a poisonous bait for molluscs comprising a molluscicidal chelate hereinbefore described.

The contact poison or poisonous bait may comprise, in addition to one or more of the present molluscicidal chelates, other components, for example other molluscicides. Such components may confer additional advantages on the contact poison or bait by, for example, synergising with the present chelates.

The present invention yet further includes with its scope a method of Killing a mollusc in which the mollusc or an environment inhabited by the mollusc is treated with a molluscicidal chelate hereinbefore described.

The present chelates are of particular interest for the control of slugs because the poisons at present used, such as metaldehyde and methiocarb suffer from a disadvantage in that a proportion of the slugs in a treated population, though at first immobilised eventually recover. At least with the present $Al^{III}$ chelates comprising ligand I, recovery is generally minimal. Environmental pollution as a result of using either the aluminium or iron chelates is, furthermore, negligible.

The present chelates, and in particular the $Al^{III}$ chelates such as $Al(acac)_3$ also offer the advantage that they do not significantly affect ground beetles such as Carabidae beetles, which are attacked by other molluscicides e.g. methiocarb.

Suitable baits normally contain in addition to the molluscicidal chelate a carrier therefor and usually comprises a mollusc food such as a cereal e.g. wheatmeal, comminuted cuttle fish, starch or gelatin, which may also serve as a carrier. A mollusc phagostimulant such as a sugar e.g. sucrose, or molasses is usually included. Non nutrient carriers of interest include non nutrient polymeric materials, pumice, carbon and materials useful as carriers for insecticides. The bait usually comprises a binder, which is suitably waterproof, such as paraffin wax or casein and may advantageously comprise a bird repellent, for example a blue colourant. In order to inhibit deterioration of the bait a fungistat may be included.

Typically the bait contains at least 3% by weight and no more than 16% by weight of molluscicide. At least when the molluscicide is an aluminium chelate the preferred concentration in the bait is 10-13% by weight.

When used as a contact poison the molluscide is typically formulated as a dust or spray, for application to foliage, soil, stubble or trash (plant residues). Examples of solid carriers include talc, chalk bentonite, clay and the like and examples of liquid carriers include water (if necessary with an emulsifier), alcohols e.g. lower alcohols such as methanol or ethanol, ketones e.g. lower ketones such as acetone or methyl ethyl ketone, liquid hydrocarbons and the like.

The treatment of both terrestrial and aquatic molluscs in accordance with the present invention is envisaged, the species *Deroceras reticulatum, Arion hortensis, Milax budapestensis, Cepaea hortensis, Helix aspersa* and *Achatina spp* being of particular interest as targets.

The invention is illustrated by the following Examples:

EXAMPLES

Laboratory Tests

Test animals

All laboratory tests were made with field-collected grey field slugs, *Deroceras reticulatum* (Pulmonata, Limacidae) and also with *Arion hortensis* in the weight range 0.4–0.6 g. They were held in polythene bowls on wet filter paper in a controlled environment cabinet cycling 12 hours light at 15° C. and 12 hours dark at 5° C. Voluntary feeding tests were made under these conditions but all other laboratory bioassays were carried out at 10° C. constant temperature with an overnight pre-treatment period also at 10° C.

EXAMPLE 1

Contact with coated glass plate

Groups of ten slugs were placed foot-down on sheets of glass, 10 cm × 10 cm, previously coated with an aqueous solution of suspension of test chemical and air dried to leave a deposit of known weight per unit area. Slugs were confined to a treated area for a period of 50 minutes at 10° C. on plates with increasing surface loadings, then removed and held in wet filter paper-floored petri dishes with food. The number of dead slugs after seven days was recorded and the values used to calculate median lethal surface concentrations ('$LC_{50}$') for each compound by probit analysis.

Results are shown In Table 1

EXAMPLE 2

Contact with treated soil surface

Groups of ten slugs were held in plastic seed trays, 20 ×34 cm × 5 cm deep, filled to a depth of 1 cm with standard soil, a sandy clay loam from Rothamsted Farm, with a pH in water of 5.2, previously oven-dried, sieved (2 mm mesh), and rewetted to field capacity tn the trays. Test chemicals were mixed with 5 g dry soil, ground together and sprinkled on to the wet soil surface. Slugs were confined to the treated surface by a 16 v pulsed DC electric fence attached to the tray sides. Trays were covered to maintain a high Relative Humidity and food was provided. Dead slugs were removed daily and the final mortality count made after 10 days.

Results as shown in Table 1.

EXAMPLES 3-13

Stomach poison action, voluntary feeding

Test chemicals were offered to slugs at a range of concentrations in a wheat-meal based formulation, groups of ten slugs being confined in 15 cm crystallising dishes containing only wet filter paper and a solid watch glass filled with 3 g (dry weight) of test bait for four 24-hour cycles of the 5° C. dark/15° C. light regime and noting weight eaten and number of animals dead after 7 days.

Results are shown in Tables II and III.

TABLE 1

Comparative toxicities of aluminium compounds on glass and on wet soil surfaces. Calculated $LC_{50}$ values of individual tests and their mean

| | | $LC_{50}(\mu g$ metal/cm$^2$) | |
|---|---|---|---|
| Compound | Test No. | On glass (50 min) | On soil (10 days) |
| Aluminium | 1 | (<40) | 82.0 |
| sulphate | 2 | 15.2 | 191.2 |
| | 3 | 17.7 | 383.9 |
| | 4 | 29.7 | 172.5 |
| | Mean | 20.9 | 207.4 |
| Al$^{III}$ | 1 | (10–100)(Example 1) | (10–100)(Example 2) |
| acetyl- | 2 | (10–100) | 45.3 |
| acetonate | 3 | | 22.9 |
| | 4 | – | 34.0 |
| | Mean | (<100) | 34.1 |

TABLE II

Effect of form and concentration of aluminium on consumption of wheatmeal bait and on slug mortality.

| | Bait eaten by 10 slugs (g Dry Wt) | | Mortality after 7 days (×/10) | |
|---|---|---|---|---|
| % Al | As aluminium sulphate | As aluminium acetyl-acetonate | (As aluminium sulphate) | (As aluminium acetyl-acetonate) |
| 0 | 0.53 | — | 3 | — |
| 0.01 | 1.31 | 1.46 (Ex. 3) | 1 | 1 |
| 0.03 | 1.08 | 0.95 (Ex. 4) | 2 | 1 |
| 0.1 | 0.62 | 0.80 (Ex. 5) | 3 | 2 |
| 0.3 | 0.89 | 0.51 (Ex. 6) | 3 | 4 |
| 1.0 | 0.41 | 0.43 (Ex. 7) | 5 | 10 |
| 3.0 | 0.42 | 0.52 (Ex. 8) | 2 | 10 |

TABLE III

Effect of metal ion concentration on consumption of aluminium acetylacetonate wheatmeal bait and on slug mortality.

| | Bait eaten by 10 slugs (g Dry Wt.) | |
|---|---|---|
| % Metal | | Mortality after 9 days (×/10) |
| 0 | 1.800 | 0 |
| 0.1 | 0.315 (Ex. 9) | 4 |
| 0.5 | 0.105 (Ex. 10) | 8 |
| 1.0 | 0.120 (Ex. 11) | 8 |
| 5.0 | 0.180 (Ex. 12) | 8 |
| 10.0 | 0.090 (Ex. 13) | 8 |

EXAMPLE 14

Field Trials

Field experiments were made on a prepared site on Rothamsted Farm, previously down to grass/clover and irrigated to increase slug numbers, and subsequently direct-drilled with winter wheat (5.11.85) after removing most of the herbage by forage harvester (16.8.85) and spraying with glycophosphate to kill the regrowth (11.9.85). The resulting soil surface was relatively undisturbed and had very little trash cover, facilitating observation of surface applications and slugs remaining above ground.

EXAMPLE 14

Field experiment 1

Treatments to control slug damage to direct-drilled winter wheat, cv. 'Avalon', were tested on plots 6 m × 8 m in four randomised blocks separated by 10 m internal headlands. Methiocarb 4 per cent bait (Draza pellets) at 5.5 kg ha$^{-1}$, and aluminium acetylacetonate 12 per cent experimental bait as 11 kg ha$^{-1}$, both produced dead and immobile slugs visible on the soil surface for several days following application on 29.12.85. They were counted (four 1 m × 1 m quadrats per plot) on the day following application and again on the third day after.

eral metals, including Copper, Zinc, Nickel, Iron and Aluminium. More detailed tests on glass plates were made with the last as its use in the field would not leave undesirable residues in the soil. The results of holding slugs in contact with increasing surface loadings of aluminium in two different chemical compounds on a glass surface for 50 minutes and on a soil surface for 10 days are given in Table 1. Mortality is expressed as a mediam lethal concentration or 'LC$_{50}$' as $\mu$g metal ion cm$^{-2}$. The results are given as LC$_{50}$ values with their 95 per cent confidence intervals for individual tests together with the mean LC$_{50}$ for all tests. Where no LC$_{50}$ value could be calculated because of incorrect choice of does range the estimated value is given in brackets.

As the sulphate on glass aluminium gave LC$_{50}$ values around 20 $\mu$g metal cm$^{-2}$.

TABLE V

Field experiment 3. Numbers of dead or immobilised slugs collected from plots treated with methiocarb or aluminium acetylacetonate baits at 5.5 kg ha$^{-1}$, and numbers which subsequently died after holding at 10° C. for a further 7 days.

| Bait | | Daily post treatment catch | | | | | | | | | | | | | | Total |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | |
| Methiocarb 4% | Collected | 0 | 2 | 0 | 2 | 38 | 3 | 11 | 2 | 1 | 0 | 0 | 0 | 0 | 0 | 59 |
| ('Draza pellets) | Died | 0 | 2 | 0 | 2 | 23 | 1 | 4 | 2 | 1 | | | | | | 35 |
| Methiocarb 4% | Collected | 0 | 1 | 0 | 5 | 28 | 4 | 6 | 2 | 3 | 0 | 0 | 0 | 0 | 0 | 47 |
| (experimental bait) Example 15 | Died | 0 | 1 | 0 | 4 | 12 | 2 | 3 | 1 | 1 | | | | | | 24 |
| Aluminium | Collected | 0 | 2 | 0 | 7 | 12 | 0 | 0 | 0 | 0 | 0 | 0 | 0 | 0 | 0 | 21 |
| acetylacetonate 4% (experimental bait) Example 16 | Died | 0 | 2 | 0 | 7 | 6 | 0 | 0 | 0 | 0 | | | | | | 15 |
| Aluimium | Collected | 2 | 8 | 0 | 9 | 54 | 0 | 13 | 2 | 3 | 0 | 0 | 0 | 0 | 0 | 91 |
| acetylacetonate 12% (experimental bait) | Died | 2 | 7 | 0 | 9 | 54 | 0 | 11 | 1 | 3 | | | | | | 87 |

Results are shown on Table IV.

TABLE IV

Field experiment 1. Numbers of slugs observed dead or immobile on plot surface one and three days after treatment with methiocarb (Draza) pellets and with an experimental molluscicide (4 quadrats 1 m$^2$ per plot × 4 plots).

| | Slugs Observed Dead or Immobile | | | |
|---|---|---|---|---|
| | +1 Day | | +3 Days | |
| Treatment | Total | n m$^{-2}$ ± SE | Total | n m$^{-2}$ ± SE |
| Methiocarb bait (Draza) @ 5.5 kg ha$^{-1}$ | 142 | 8.9 ± 0.94 | 189 | 11.8 ± 2.28 |
| Aluminium acetylacetonate bait @ 11.0 kg ha$^{-1}$ | 374 | 23.4 ± 5.05 | 214 | 13.4 ± 2.64 (Ex. 14) |

EXAMPLES 15 and 16

Field experiment 3

The number of slugs killed or immobilised by proprietary 4 per cent methiocarb bait (Draza pellets), methiocarb 4 per cent experimental bait, aluminium acetylacetonate 4 per cent experimental bait and 12 per cent experimental bait, all applied at 5.5 kg ha$^{-1}$ to 0.5 m × 1 m areas of the winter wheat field, was compared over a 14-day period from 4.1.86. Plots were separated by 5 m. Each treatment was replicated eight times in two 4×4 latin squares. Dead or immobile slugs were again collected daily and held for 7 days at 10° C.

Results are shown in Table V.

Notes on the results

A. Laboratory tests.

Preliminary tests exposing slugs to simple metal salts on a glass surface indicated significant toxicity in sev- When applied to a wet soil surface the activity of all the compounds was greatly reduced despite the increase in exposure time from 50 minutes to 10 days. The reduction in activity was not the same for all compounds.

When offered sweetened wheatmeal bait containing increasing concentrations of aluminium as sulphate or acetylacetonate in non-choice tests the amount eaten fell with increasing concentration. Similar weights of bait were eaten regardless of the form of aluminium used, but mortality was much greater with the chelated aluminium bait, reaching 100 per cent at 1 per cent Aluminium content (Table II).

When offered sweetened wheatmeal bait containing aluminium acetylacetonate over a range of concentrations of metal ion up to 10 per cent, consumption was again depressed with increasing proportion of poison. The optimum concentration of aluminium acetylacetonate lay in the range 0.5 to 5.0 per cent of aluminium (Table III).

B. Field Experiment 1

The mean number of slugs dead or immobilised on the surface of the 6×8 m plots on the day following treatments begun on 29 October suggests than the aluminium acetylacetonate experimental bait at 11 kg ha$^{-1}$ was the most effective treatment, catching 23.4 slugs m$^{-2}$. Commercial methiocarb 4 per cent bait (Draza pellets) at the manufacturers' recommended rate of 5.5 kg ha$^{-1}$ caught 8.9 slugs m$^{-2}$. A second count after a further two days had passed confirmed this order although the differences were less. The results of the second count are less reliable. (Table IV).

Field Experiment 3

In this comparison of methiocarb and aluminium acetylacetonate, all bait was applied at the same rate, 5.5 kg ha$^{-1}$, and the two poisons were also compared in the same experimental bait carrier at the same concentration of poison. Weather adverse to slug activity and the lower application rate reduced the numbers of slugs caught overall. 4 per cent methiocarb as Draza caught more slugs then 4 per cent methiocarb in the experimental bait, but 12 per cent aluminium acetylacetonate (1 per cent Aluminium) in experimental bait, caught most slugs. On holding for recovery only 4/91 (4.4 per cent) of the slugs which ingested the 12 per cent aluminium acetylacetonate bait resumed normal activity, although at the lower concentration (3 per cent al) 6/21 (28.6 per cent) did so.

Of the methiocarb (experimental bait) - poisoned slugs 23/47 (48.9 per cent) recovered, while 24/59 (40.7 per cent) of those poisoned by methiocarb (Draza bait) did so (Table V).

EXAMPLE 17

Laboratory tests where 3 replicates of 10 slugs were confined with standard baits containing 1% metal ion in different compounds, and no alternative food supplied, gave the following results:

Aluminium sulphate (Al$_2$(SO$_4$)$_3$): 0/10, 0/10, 0/10 killed

Aluminium acetylacetonate: 10/10, 10/10, 10/10 killed (Ex 17)

EXAMPLE 18

A field trial, where baits were placed among a growing wheat crop and the numbers of slugs 'caught' recorded over 11 days, gave these results:

| | | |
|---|---|---|
| Methiocarb 4% (Bayer 'Draza' pellets) | 21 | caught |
| Methiocarb 4% (RES Standard Bait)* | 19 | " |
| Metaldehyde 6% (Pan Britannica Ind. Mini pellets) | 32 | " |
| Metaldehyde 6% (RES Std. Bait)* | 50 | " |
| Al$_2$(SO$_4$)$_3$ (1% Aluminium) (RES Std. Bait)* | 0 | " |
| Al(acac)$_3$ (1% Aluminium) (Res Std. Bait) | 41 | " (Ex 18) |

*RES: Rothamsted Experiment Station: See Examples 19-22

EXAMPLES 19-22

Bioassay Method

Test compounds were incorporated into a standard wheat-flour-based edible carrier containing 10% paraffin wax binder and 2.5% sucrose phagostimulant, in increasing concentrations 0, 1, 4, 7, 10, 13 and 16% a.i.

Groups of ten field-collected *D. reticulatum* in the weight range 400–600 mg were confined with 0.5 g DM test bait at each concentration for a period of 4 days under a regime of 12 h dark @ 5° C. and 12 light @ 15° C. Weight of bait eaten and number of slugs killed were recorded. Each group of compounds was tested against a concurrently run Al(ac.ac)$_3$ standard bait.

The results are shown in Table VI. In Examples 23 to 35, where six groups of ten slugs are offered bait containing 1,4,7,10,13 or 16% a.i., have been reduced to two values, the total amount of a.i. ingested (mg) which gives an indication of the palatability of the compound, and (ii), the total number of slugs killed (×/60) which, with (i), gives an indication of its relative toxicity.

In Table VII there is presented a comparison of the efficacy of present iron and aluminium chelates with metaldehyde and methiocarb under field conditions (grass/clover).

TABLE VI

Effect of increasing concentrations of iron and aluminum chelates in a standard bait on feeding and kill of *Deroceras reticulatum*

| Example | Compound | a.i. (%) | Eaten (%) | Kill (x/60) |
|---|---|---|---|---|
| 19 | Tris (2,4-pentanedionato) Al III | 0 | 100 | 0 |
| | | 1 | 100 | 0 |
| | | 4 | 44 | 0 |
| | | 7 | 29 | 6 |
| | | 10 | 20 | 7 |
| | | 13 | 19 | 8 |
| | | 16 | 20 | 8 |
| 20 | Tris (2,4-hexanedionato) Al III | | 100 | 0 |
| | | | 100 | 1 |
| | | | 100 | 0 |
| | | | 58 | 4 |
| | | | 29 | 1 |
| | | | 26 | 5 |
| | | | 22 | 5 |
| 21 | Tris (3,5-heptanedionato) Al III | | 100 | 0 |
| | | | 100 | 1 |
| | | | 100 | 3 |
| | | | >10 | 0 |
| | | | >10 | 1 |
| | | | >10 | 1 |
| | | | >10 | 2 |
| 22 | Tris (N-nitroso-N-methyl hydroxylaminato) Fe III | | 100 | 2 |
| | | | 17 | 5 |
| | | | 11 | 8 |
| | | | 4 | 5 |
| | | | 8 | 5 |
| | | | 5 | 7 |
| | | | 7 | 8 |

| Example | Compound | a.i. ingested (mg/60 slugs) | Slugs dead (x/60) |
|---|---|---|---|
| 23 | Tris (2,4-pentanedionato) Al III | 61 ±4.6 | 35 ±1.4 |
| 24 | Tris (2,4-hexanedionato) Al III | 94 | 16 |
| 25 | Tris (3,5-heptanedionato) Al III | 15 | 8 |
| 26 | Tris (2,4-heptanedionato) Al III | 21 | 4 |
| 27 | Tris (1-methoxy-2,4-pentane dionato) Al III | 40 | 10 |

TABLE VI-continued
Effect of increasing concentrations of iron and aluminum chelates in a standard bait on feeding and kill of *Deroceras reticulatum*

| | | | |
|---|---|---|---|
| 28 | Tris (N-nitroso-N-methyl hydroxylaminato) Fe III | 17 | 38 |
| 29 | Tris (1-dimethoxy-2, 4-pentanedionato) Al III | 35 | 14 |
| 30 | Tris (N-nitroso-N-ethyl hydroxylaminato) Fe III | 6 | 49 |
| 31 | Tris (N-nitroso-N-n-propyl hydroxylaminato) Fe III | 50 / 55 | 58 / 58 |
| 32 | Tris (N-nitroso-N-2-propyl hydroxylaminato) Fe III | 3 | 43 |
| 33 | Tris (N-nitroso-N-n-butyl hydroxylaminato) Fe III | 53 | 37 |
| 34 | Tris (N-nitroso-N-2-butyl hydroxylaminato) Fe III | 54 | 46 |
| 35 | Tris (N-nitroso-N-2-methylpropyl hydroxylaminato) Fe III | 160 | 42 |

TABLE VII

| Example No. | Bait Poison Compound of Example No. | % ai | % sucrose | Day 1 D | Day 1 I | Day 2 D | Day 2 I | Day 3 D | Day 3 I | Day 4 D | Day 4 I | Total D + I |
|---|---|---|---|---|---|---|---|---|---|---|---|---|
| 36 | 28 | 10 | 2.5 | 81 | 4 | 117 | 19 | 137 | 34 | 162 | 40 | 202 |
| 37 | 30 | 10 | 2.5 | 127 | 77 | 194 | 33 | 254 | 51 | 313 | 54 | 367 |
| 38 | 31 | 10 | 2.5 | 103 | 30 | 137 | 52 | 165 | 75 | 193 | 82 | 275 |
| 39 | 33 | 10 | 2.5 | 22 | 43 | 41 | 60 | 47 | 89 | 58 | 89 | 147 |
| 40 | 34 | 10 | 2.5 | 37 | 34 | 42 | 48 | 42 | 85 | 45 | 86 | 131 |
| — | Metaldehyde | 10 | 2.5 | 126 | 33 | 139 | 142 | 241 | 161 | 271 | 190 | 461 |
| — | Metaldehyde (PP pellets) | 6 | — | 38 | 137 | 46 | 224 | 69 | 317 | 86 | 368 | 454 |
| — | Methiocarb | 10 | 2.5 | 9 | 244 | 10 | 371 | 11 | 499 | 16 | 541 | 557 |
| — | Methiocarb (Draza pellets) | 4 | — | 5 | 195 | 9 | 197 | 12 | 331 | 14 | 390 | 404 |
| 41 | Al (acac)$_3$ | 10 | 2.5 | 210 | 13 | 294 | 54 | 378 | 86 | 435 | 98 | 533 |
| 42 | Al (acac)$_3$ | 10 | 5 | 185 | 11 | 266 | 27 | 354 | 57 | 419 | 66 | 485 |
| 43 | Al (acac)$_3$ | 10 | 10 | 186 | 7 | 276 | 26 | 338 | 51 | 396 | 64 | 460 |

—Results of first 4 days of trial

The Examples demonstrate the use as a molluscicide of a chelate of aluminum (III) with a ligand of formula (I) or of iron (III) with a ligand of formula (II). This use comprises treating molluscs or an environment inhabited by molluscs with a molluscicidally effective amount of the chelate, such as by applying to such environment a molluscicidal composition comprising a molluscicidally effective amount of the chelate and a carrier therefor.

The amount of the molluscicidal chelate of the invention to be used will depend upon the degree of infestation, the environmental conditions and the particular chelate used, and can be derived as in known, from the $LC_{50}$ value of the particular molluscicidal chelate to be used. Presently, it is considered that useful rates of application of the molluscicidal chelate of the invention will provide from about 0.1 kg ha$^{-1}$ to about 3.0 kg ha$^{-1}$ of the chelate when the chelate is applied as a poison bait and from about 20 kg ha$^{-1}$ to about 80 kg ha$^{-1}$ of the chelate, when the chelate is applied as a dust or spray. As is known, the amounts to be used for any particular application may be more or less than set forth above and multiple applications may be desirable.

We claim:

1. A method of killing molluscs, which comprises treating molluscs or an environment inhabited by molluscs with a molluscicidally effective amount of a chelate of iron (III) with a ligand of formula II $$[R^3NO.N{=}O]^-  \qquad\qquad II$$

wherein in formula II $R^3$ represents $C_1$-$C_6$ alkyl, provided that when $R^3$ is alkyl containing more than four carbon atoms, said alkyl is branched chain alkyl.

2. The method according to claim 1, wherein a molluscicidal composition comprising a molluscicidally effective amount of said chelate and a carrier therefor is applied to said environment inhabited by said molluscs.

3. The method according to claim 2, wherein said molluscicidal composition is a poison bait.

4. The method according to claim 2, wherein said molluscicidal composition is a contact poison.

5. The method according to claim 4, wherein said contact poison is a dust or spray.

6. The method according to claim 1, wherein a molluscicidal composition comprising a molluscicicidally effective amount of said chelate and a carrier therefor is applied to said molluscs.

7. The method according to claim 6, wherein said molluscicidal composition is a contact poison.

8. The method according to claim 7, wherein said contact poison is a dust or spray.

9. The method according to claim 1, in which $R^3$ contains no more than four carbon atoms.

10. The method according to claim 1, in which $R^3$ is methyl, ethyl, or n-propyl.

11. The method according to claim 1, in which said chelate comprises a ligand formed by loss of a proton from a compound selected from the group consisting of
$CH_3NOH.N=O$,
$CH_3CH_2NOH.N=$),
$Ch_3CH_2CH_2NOH.N=O$,
$(CH_3)_2CHNOH.N=O$,
$CH_3(CH_3)_2CH_2NOH.N=O$,
$CH_3CH_2CH(CH_3)NOH.N=O$, and
$(CH_3(_2CH_2CH_2NOH.N=O$.

12. The method according to claim 1, in which said chelate is of the formula $FE^{III}[CH_3NON=O]_3$ or $Fe^{III}[CH_3CH_2NON=O]_3$ or $Fe^{III}[CH_3CH_2CH_2NON=O]_3$.

13. A molluscicidal composition, comprising a molluscicidally effective amount of a chelate of iron (III) with a ligand of formula II $$[R^3NO.N=O]^-  \qquad \text{II}$$

wherein in formula II $R^3$ represents $C_1$-$C_6$ alkyl, provided that when $R^3$ is alkyl containing more than four carbon atoms, said alkyl is branched chain alkyl, and a carrier therefor.

14. The composition according to claim 13, in the form of a contact poison.

15. The composition according to claim 14, wherein said contact poison is a dust or spray.

16. The composition according to claim 13, in the form of a poison bait.

* * * * *